United States Patent [19]

Ferguson

[11] Patent Number: 5,520,926
[45] Date of Patent: May 28, 1996

[54] METHOD OF USING MANNOSE PHOSPHATES FOR THE TREATMENT OF FIBROTIC DISORDERS

[75] Inventor: Mark W. J. Ferguson, Heaton Moor, England

[73] Assignee: British Technology Group Limited, London, England

[21] Appl. No.: 290,939

[22] PCT Filed: Mar. 16, 1993

[86] PCT No.: PCT/GB93/00541

§ 371 Date: Aug. 24, 1994

§ 102(e) Date: Aug. 24, 1994

[87] PCT Pub. No.: WO93/18777

PCT Pub. Date: Sep. 30, 1993

[30] Foreign Application Priority Data

Mar. 17, 1992 [GB] United Kingdom .................. 9205800

[51] Int. Cl.$^6$ .................................................. A61K 9/70
[52] U.S. Cl. .......................... 424/443; 424/422; 424/444; 424/445; 424/446; 424/447; 424/448; 424/449; 514/23
[58] Field of Search .................................. 424/443, 422, 424/444–449, 400; 514/23

[56] References Cited

U.S. PATENT DOCUMENTS

| | | | |
|---|---|---|---|
| 4,703,040 | 2/1987 | Markov | 514/23 |
| 4,889,844 | 1/1989 | Silvetti et al. | 514/60 |

FOREIGN PATENT DOCUMENTS

| | | |
|---|---|---|
| 230023 | 4/1987 | European Pat. Off. . |
| 221728 | 5/1987 | European Pat. Off. . |
| 241818 | 10/1987 | European Pat. Off. . |
| 91/55319 | 1/1984 | Japan . |
| 05/058868 | 11/1993 | Japan . |
| 1311956 | 4/1973 | United Kingdom . |
| 2092001 | 3/1982 | United Kingdom . |
| WO90/01938 | 12/1990 | WIPO . |
| WO91/09604 | 1/1991 | WIPO . |
| WO91/04748 | 3/1991 | WIPO . |
| WO92/17206 | 10/1992 | WIPO . |
| WO93/19783 | 10/1993 | WIPO . |

OTHER PUBLICATIONS

Owaku et al., *Chemical Abstracts*, vol. 106, #89993 (1985).
P A Dennis and D B Rifkind, "Cellular activation of latent transforming growth factor β. . . ", Proc. Natl. Acad. Sci. USA 88, 580–584 (1991).
M N Lioubin et al., "Characterization of Latent Recombinant TGF–β2 Produced by Chinese Hamster Ovary Cells" Journal of Cellular Biochemistry 45, 112–121 (1991).
K Miyazono et al. "Latent Forms of TGF–β : Structure and Biology", Annals N.Y. Acad. Sci. 593, 51–58 (1990).
K Miyazono and C–H. Heldin, "Latent Forms of TGF–β : molecular structure and mechanisms of activation", Ciba Foundation Symposium 157, 81–92 (1991).
E J Kovacs, "Fibrogenic cytokines : the role of immunemediators in the development of scar tissue", Immunology Today 12 (1), 17–23 (1991).
K Miyazono et al., "Role for carbohydrate structures in TGF–β1 latency" Nature 338, 158–160 (1989).
L Storckenfeldt et al., "Stimulatory effects of insulin like growth factor II on DNA synthesis in the human embryonic cornea", Cell Biology International Reports 15 (12) 1217–1233 (1991).

(List continued on next page.)

Primary Examiner—Thurman K. Page
Assistant Examiner—Pamela S. Webber
Attorney, Agent, or Firm—Nixon & Vanderhye

[57] ABSTRACT

Mannose-6- and 1-phosphates and their pharmaceutically acceptable salts and bioprecursors thereof are useful in the treatment of fibrotic disorders. They accelerate wound healing and the 6-phosphate prevents or mitigates scar formation. The invention includes particular, appropriate formulations of the mannose phosphate.

10 Claims, 1 Drawing Sheet

OTHER PUBLICATIONS

Scars and Stripes, The Newsletter of the Wound Healing Society (The Wound Healing Center, Richmond Va. 23298–0117), vol. 2 No. 3 Spring 1992 (Mailed Feb. 7, 1992), pp. 4–6.

D. M. Foreman et al., "The effect of mannose–6–phosphate on healing adult rodent dermal wounds", European Tissue Repair Society, Second Annual Meeting, Aug. 26–28 1992, Malmo, Sweden, Abstract 15, p. 26.

M. W. J. Ferguson, "Control of Scarring in Adult Wounds", American College of Surgeons, 78th Annual Clinical Congress, Oct. 11–16 1992, New Orleans, No. 22, pp. 36 & 37.

M. W. J. Ferguson, "Fetal Wound Healing: Clinical Implications", American College of Surgeons, 78th Annual Clinical Congress, Oct. 11–16, 1992, New Orleans, No. 13, pp. 47 & 48.

Letter of Aug. 7, 1992 from Prof. M. W. J. Ferguson to Dr. D. B. Rifkin and reply dated Aug. 19, 1992 from Dr. D. B. Rifkin to Prof. M. W. J. Ferguson.

Letter of Sep. 9, 1992 from Prof. M. W. J. Ferguson to Dr. C–H. Heldin and reply dated Sep. 16, 1992 from Dr. C–H. Heldin to Prof. M. W. J. Ferguson.

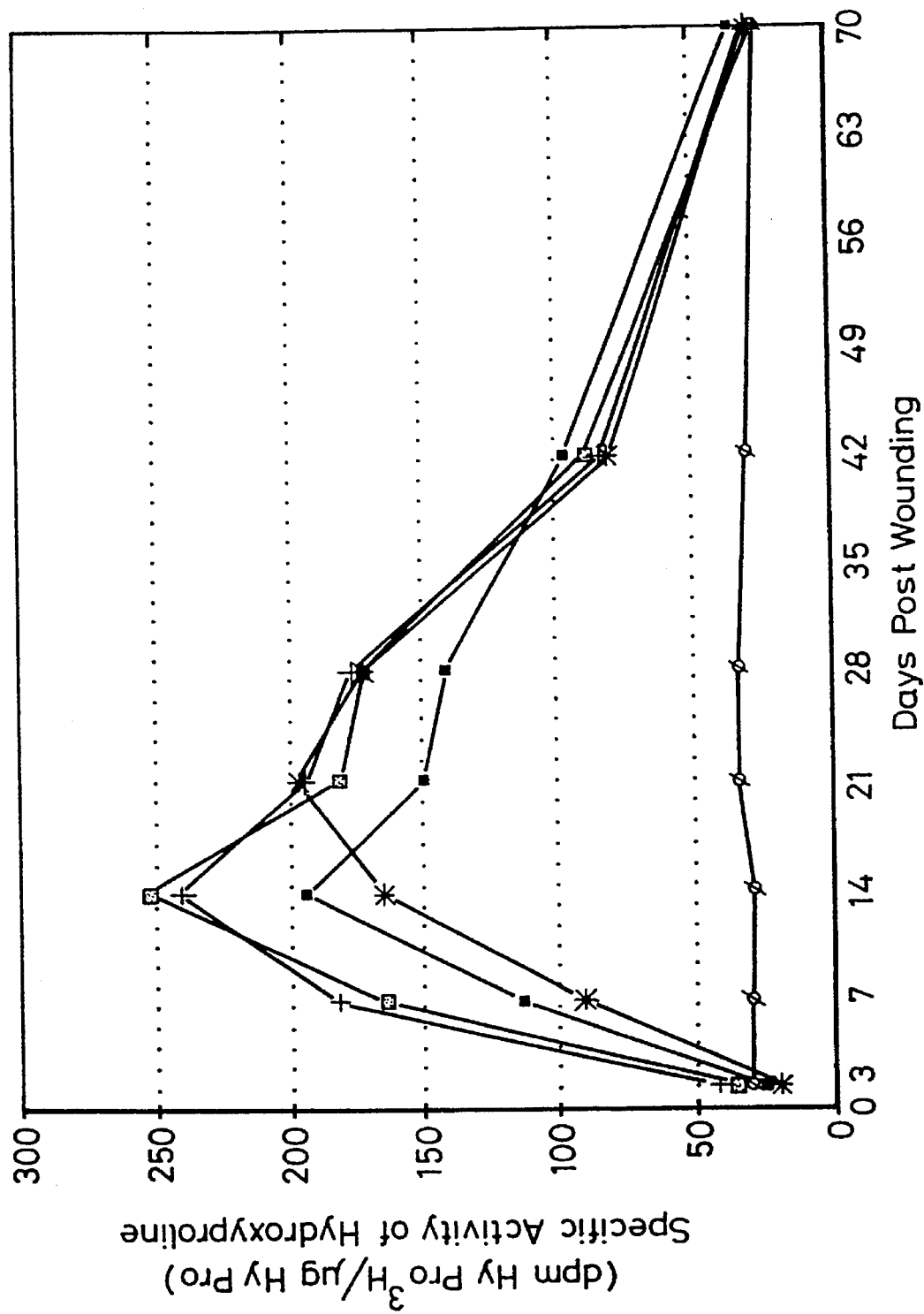

METHOD OF USING MANNOSE PHOSPHATES FOR THE TREATMENT OF FIBROTIC DISORDERS

BACKGROUND OF THE INVENTION

1. Field of the Invention

This invention relates to the use of certain known compounds for the novel purpose of healing wounds and treating certain other conditions associated with the accumulation of extracellular matrix In tissue.

2. Description of the Related Art

It is a problem that although wounds in humans and other mammals usually heal reasonably quickly, unsightly scar tissue is often formed. It is known that growth factors are implicated in fibrotic disorders. Various proposals have been made to ameliorate the effects of fibrotic disorders by administering either the growth factor or antibodies thereto. See, for example W. A. Border et al., Nature 346 371–374 (1990), who showed that extracellular matrix production in acute mesangial proliferative glomerulonephritis (inflammation of the kidney believed caused by immunological injury to cells) is associated with increased production of transformIng growth factor (TGF)-β1 and suppressed by administering anti-TGF-β1. E. Kovacs, Immunology Today 12 (1) 17–23 (1991) concludes that blocking the effects of certain cytokines (such as TNF-α) with antibodies has diminished fibrosis in animal models of tissue injury. PCT Application Publication No. WO91/04748 (La Jolla Cancer Research Foundation) proposes to treat pathologies associated with accumulation of extracellular matrix in tissue with platelet derived growth factor (PGDF) or with antibodies to TGF-β1. The diseases treated are in general fibrotic diseases and include glomerulonephritis, adult respiratory distress syndrome, cirrhosis of the liver, fibrocytic disease, fibrosis, fibrotic cancers, fibroids, fibroadenomas and fibrosarcomas. Other fibrotic conditions are mentioned. Also, the method can be used to treat or prevent excessive scarring such as keloid scars (hard, irregular scar tissue in the skin which forms when a wound is under tension) and/or is produced in genetically pre-disposed people. H. Shah, D. H. Foreman and M. W. J. Ferguson, The Lancet 339, 213–214 (Jan 25, 1992), describe the control of scarring in wounds by administering antibody which neutralises TGF-β1 and -β2.

The biological mechanisms by which the growth factors operate is not well understood, see C. C. Bascom et. al., Molecular and Cellular Biology 9, 5508–5515 (1989).

It is known that TGF-β1 is synthesised as a pre-pro-protein of 390 amino acids which is converted to mature protein by cleavage between aa residues 278 and 279. However, TGF-β1 isolated in vivo is found predominantly as a high molecular weight latent complex (LTGF β1) in which the pro-region is still associated with the mature molecule, despite the cleavage of the peptide bond. TGF-β2 and β-3 also have latent forms. All have been shown to bind to a plasma membrane receptor called the cation-independent mannose-6-phosphate/insulin-like growth factor II receptor. Binding occurs through mannose-6-phosphate residues attached at glycosylation sites within the pro-region and, in the case of TGF-β1 and TGF-β2, has been shown to be inhibited by antibodies to the receptor. In the case of TGF-β1, binding is inhibited by mannose-6-phosphate itself. See P. A. Dennis and D. B. Rifkin, Proc. Natl. Acad. Sci. USA, 88, 580–584 (1991), M. N. Lioubin, H. Marquardt, R. Roth, K. S. Kovacina and A. F. Purchio, Journal of Cellular Biochemistry 45, 112–121 (1991) and K. Miyazano et al., Annals of the New York Academy of Sciences 593, 51–58 (1990). It has not been clear whether it is desirable to prevent the generation in vivo of the mature active forms of TGFs or whether mannose-6-phosphate receptor binding is the only means of activating the mature protein. It has been suggested in the literature that TGF-β1 becomes activated under various pH conditions: see "The Transforming Growth Factor βs" in "Peptide Growth Factors and Their Receptors 1" (eds. M. B. Sporn and A. B. Roberts), Springer Verlag 1990, pages 419–472, at page 432, and references cited therein. See also K. Miyazano et. al., supra, at page 55, who mention activation by enzymes such as plasmin, cathepsin D and a glycosldase. These authors also suggest that high concentrations of sialic acid or mannose-6-phosphate activate the latent form.

Further prior art, the relevance of which is not apparent without knowledge of the invention, is mentioned below after the "Summary of the invention" section.

SUMMARY OF THE INVENTION

It has now been found that mannose-6-phosphate (M-6-P) is useful in promoting (accelerating) wound healing, while mitigating or preventing formation of scar tissue. The term "mannose" refers herein exclusively to the natural D-isomer. Also, mannose-1-phosphate is useful in promoting wound healing, although it does not necessarily have any anti-scarring effect. The mannose phosphate (a term used herein collectively to refer to the 6- and 1-phosphates) can be used as such, as a pharmaceutically acceptable salt, e.g. a monosodium or disodium salt, or in any bioprecursor or "pro-drug" form effective to release the mannose phosphate into the wound area.

The invention therefore includes the novel use as aforesaid, expressed in whatever terms are conventional in the patent laws of the appropriate countries where patent applications are being filed. It also includes particular formulations for this purpose, notably a cream or gel (which includes a vehicle or carrier), a sterile solution (which includes a physiologically acceptable diluent) and wound dressings and implant materials incorporating the mannose phosphate as aforesaid.

ADDITIONAL DESCRIPTION OF PRIOR ART

PCT Patent Application publication WO 90/01938 (Australian National University) relates to the use of sugar phosphates, especially mannose-6-phosphate or glucose-1-phosphate, for anti-inflammatory or immunosuppresive treatments. The term "anti-inflammatory" as used therein does NOT mean the reduction of swellings caused by bruises, insect bites etc., but rather refers to the action of the agents against suspected autoimmune diseases, including multiple sclerosis and rheumatoid arthritis, and against graft-host rejection.

PCT Patent Application WO 91/09604 (Perstorp AB) relates to the use of any of a huge class of sugar phosphates, including mannose-6-phosphate, to treat a huge variety of conditions including tissue damage such as oedema formation, vascular leakage, burns, and damage (unspecified) to the eye retina. There are no examples and the entire document is obviously lacking in scientific credibility.

Other, even less relevant, prior art comprises the following patent specifications:

EP-A 230 023 (Marion Laboratories Inc.) refers to polysulphated polysaccharides for enhancement of wound healing, one example being mannose pentasulphate; EP-A 221 728 (Silvetti) proposes a composition of a monosaccharide, e.g. mannose and a starch hydrolysate for wound healing; U.S. Pat. No. 4,889,844 (Silvetti) is similar in disclosure but has more limited claims; GB-A 2 048 070 relates to a wound healing composition containing a sugar suitably in the form purchased at any grocery store, preferably sucrose, and an anti-bacterial agent, e.g. povidone/ iodine; GB-A 2 092 001 relates to the use of sodium fructose-1,6-diphosphate to treat burns patients; U.S. Pat No. 4,703,040 uses fructose-1, 6-diphosphate to treat adult respiratory distress syndrome; Japanese Patent Application Publication No. 25447/1984 (Nisshin Flour Milling) relates to a long-chain hydrocarbyl phosphate derivative of mannose-1-phosphate as a carcinostatic agent.

The above prior art needs to be viewed in the light of the finding in connection with the present invention, based on animal tests, that glucose, galactose, mannose, glucose-6-phosphate; galactose-6-phosphate and glycerol-3-phosphate have no discernible effect on wound healing.

BRIEF DESCRIPTION OF THE DRAWINGS

The FIGURE is a graph of counts of radiolabelled hydroxyproline, a measure of collagen synthesis and deposition against time after the wounding, for wounds in rats treated with mannose-6- or 1-phosphate, glucose and a control.

DESCRIPTION OF THE PREFERRED EMBODIMENTS

The mannose-6-phosphate used in this invention is of formula (1) wherein one of $R^1$ and $R^2$ is hydrogen and the other is phosphoryl, $PO(OH)_2$.

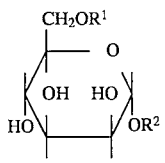

(1)

It can be administered in the form of the free phosphoric acid or a pharmaceutically acceptable mono- or di- salt thereof, for example a sodium, calcium, magnesium or barium salt. It can also be in the form of a bioprecursor, i.e. a compound which is converted in situ (after application to the body) to the mannose phosphate. This could be achieved, for example, by linking a sugar alcohol group of the mannose phosphate to an appropriate acid to form an ester, in which this ester linkage is more readily hydrolysable than the phosphate linkage of mannose phosphate. Other forms of compound which will release mannose phosphate under hydrolyric, enzymatic or other conditions prevailing in the appropriate location in the body of the fibrotic condition to be treated, especially in wounds in the skin, will be evident to chemists and are encompassed in the definition of the mannose phosphate for the purposes of this invention.

In wound healing it is contemplated that it will be desirable to apply the mannose phosphate to the wound rapidly, i.e. as soon as possible after the incision, injury, etc., normally within 48 hours, preferably within 24 hours and most preferably within 12 hours. It is belleved desirable to maintain a fairly constant concentration of the mannose phosphate in the wound area for several days, e.g. up to 3 or 4 days, after wounding. A sustained release formulation of the mannose phosphate is therefore preferable. Very slow release formulations of the mannose phosphate are likely to be largely inappropriate, although formulations which allow a quick release of the threshold concentrations and thereafter slow release might be appropriate in some circumstances, in any case, slow release likely to be useful in treating other fibrotic disorders.

Preferred formulations of the mannose phosphate in this invention include creams, ointments and gels which can be formulated in any conventional way with aqueous or oleaginous vehicles or carriers, which may also include antiseptics and other agents conventional in wound treatment; sterile injectable solutions which can be formulated with any appropriate conventional diluent, especially physiological saline; sterile syringeable solutions of the mannose phosphate and hyaluronic acid or other polymeric fluid carrier or diluent; lotions and pastes. A particularly convenient way of applying the mannose phosphate will be by way of an impregnated wound dressing, such as a bandage, plaster, absorbent pad or polymeric or hydrogel dressing, e.g. of collagen, hyaluronic acid, sodium alginate or polyvinyl chloride. The mannose phosphate is incorporated in the dressing, e.g. by impregnation, and will normally be stored under sterile conditions, ready for use. For internal treatments, an implant comprising a polymer, as carrier, and the mannose phosphate is suggested. Mannose-6-phosphate and, it is believed, mannose-1-phosphate are stable to hydrolysis in solutions, gels and other wet forms provided that the conditions are not alkaline.

Although the invention is primarily of interest in relation to skin wounds, whether arising through surgery or otherwise, including severe abrasions lacerations and burns, it is also applicable to fibrotic skin disorders, e.g. photo-damage (which is believed to up-regulate certain effectors of an increase in fibrous tissue) and irritancy and to the other disorders hereinbefore mentioned in connection with PCT Application Publication WO 91/04748 (La Jolla), the disclosure of which in relation thereto is herein incorporated by reference. Incidentally, claim 1 of the La Jolla application calls for contacting the tissue in which extracellular matrix has accumulated with an agent which suppresses the extracellular matrix producing activity of TGF-β. The mannose phosphate used in the present invention appears not to fall within this definition.

A particularly important aspect of the invention lies in the treatment of fibrotic disorders of the eye, especially those leading to glaucoma or epi-retinal membrane formation where a tear in the eye tissue leads to fibrosis with contraction and wrinkling of the retina. The invention includes sterile eyedrop solutions of the mannose phosphate, preferably the 6-phosphate, or salt or bioprecursor thereof.

The healing of ligaments is also improved by the mannose phosphate, preferably the 6-phosphate or salt or bioprecursor thereof.

The mode of application of the mannose phosphate will normally be topical, e.g. to a wound (inside and/or around it), but in appropriate cases subcutaneous or intradermal injection or implantation may be required in order better to reach the affected tissue. In extreme cases intramuscular or intravenous injection may be advisable. Preliminary data suggest that low or moderate concentrations of mannose-6-phosphate are required in order to accelerate and reduce scarring in wound healing. Preferably the mannose phosphate is applied in 10–60 mM concentration to the affected area at least twice per day for at least the first three days of treatment.

The following Examples illustrate the invention. The phosphates referred to herein were in the form of their monsodium salts except glycerol-3-phosphate in Example 6 which was as the disodium salt.

EXAMPLE 1

Four incisional wounds 1 cm long were made in the flanks of adult Sprague Dawley rats. Each wound extended to the depth of the underlying parniculous carnosis. In each animal one wound was left untreated as a control. The other three wounds were treated by subcutaneous and intradermal injection of the surrounding skin with mannose-6-phosphate in sterile physiological saline, glucose-6-phosphate and mannose-1-phosphate respectively. Each wound was treated three times, on days 0, 1 and 2 after wounding. The rats were treated with six different concentrations of each reagent, namely 0.5, 1, 5, 20, 50 and 100 millimolar per animal per injection. All the rats were killed 7 days after wound healing and the wounds were excised. The wound tissue was snap-frozen in liquid nitrogen, cryo-sectioned and stained with various antibodies to detect macrophages and monocytes (indicators of the inflammatory response), to laminin (an extracellular matrix molecule which stains basement membranes and highlights new blood vessel formation in the wound), to fibronectin (an early extracellular matrix molecule, giving an indication of the amount of extracellular matrix molecules present and their orientation) and to collagen (the principal constituent of scar tissue).

The results showed that mannose-6-phosphate at 20 mM gave the best results accelerated healing, good orientation of collagen fibres, with restitution of the normal dermal architecture, followed closely by the same agent at 50 mM. Lower concentrations gave little effect, presumably through inadequate dosage. On the other hand, 100 mM gave a poor result, worse than the control.

Mannose-1-phosphate performed better than the control. It accelerated wound healing but had no effect on scarring. The collagen fibres were badly oriented and there was no effect on monocytes and macrophages.

Glucose-6-phosphate gave slightly accelerated wound healing but not as much as either mannose phosphate.

EXAMPLE 2

Mannose-6-phosphate (M-6-P), mannose-1-phosphate (M-1-P) and glucose (G) at 20 mM were injected into separate incisional wounds in rats for 3 days as described in Example 1. There was also a control non-injected wound. Glucose was used for comparison, representing a non-phosphorylated sugar. Wounds were harvested at 3 days and at 1, 2, 3, 4, 6 and 10 weeks. The results confirmed that M-6-P and M-1-P accelerated wound healing, as shown by earlier deposition of collagen within wounds. Moreover, the M-6-P-treated wounds had slightly increased monocyte and macrophage numbers (averaging 249 monocytes and macrophages/1 week old wound compared to 201 in control wounds). The wounds of the M-6-P-treated animals examined after 4, 6 and 10 weeks showed improved organisation and orientation of the collagen fibres in the dermis than those of the M-1-P- and G-treated wounds. The G-treated wounds were retarded in healing compared with controls and showed slightly increased scarring compared with controls.

EXAMPLE 3

Wounds were injected with 20 mH M-6-P, M-1-P and G for 3 days as described previously. A control, non-injected wound was also used. Rats were labelled with $^3$H-hydroxyproline (1 µCi/3.74 g) intraperitoneally, each at 24, 16 and 8h before wound harvest. Wounds were harvested under microscope with 1 mm surrounding tissue at 3 days, 1, 2, 3, 4, 6 and 10 weeks. Control (normal skin) samples were also taken. Samples were then weighed. The FIGURE is a plot of the specific activity of the labelled hydroxyproline in decays/minute/microgram of hydroxyproline for the excised wounds, against the time of wound harvest. Since the label was available for incorporation no longer than 24 hours before killing, the specific activity of the hydroxyproline reflects the net rate of synthesis and deposition of collagen during this 24 hour period. 3 days after wounding, the rates for the wounds and the control were the same. The rate of new collagen deposition in the control wound (filled square) increased rapidly to a maximum around the fourteenth day and remained elevated until the sixth week, before returning to the level of the normal skin control (greek phi symbol) by week ten. Both M-6-P (+) and M-1-P (larger, shaded squares) increased collagen deposition in the healing wound for 28 days post-wounding, before reducing to control wound levels. By contrast, addition of glucose (*) slightly reduced the amount of collagen deposited for the first 2 weeks after wounding, before slightly increasing collagen between 3 and 4 weeks.

EXAMPLE 4

To determine whether phosphorylation was necessary, mannose (unphosphorylated) and glyceraldehyde-3-phosphate (G-3-P) were used in healing studies. Nounds were injected with 20 mM mannose and 20 mM G-3-P for 3 days, as described previously, and harvested after 7 and 14 days. Both these molecules gave similar results to glucose, i.e. delayed the wound healing response, suggesting that phosphorylatlon of mannose is required for accelerated healing, and gave no anti-scarring activity.

EXAMPLE 5

This Example shows the effects of increasing the frequency of application to the wound.

Experimental rats were wounded as described earlier and the wounds treated with nothing (control), 20 mM mannose-6-phosphate (M-6-P) 20 mM mannose-1-phosphate (M-1-P) or 20 mM mannose. However, instead of being given a single injection on days 0, 1 and 2, wounds were injected every 8 hours on days 0, 1 and 2. wounds were harvested after 7 and 14 days and processed for histology and immunocytochemistry.

As previously, mannose-6-phosphate (M-6-P) accelerated wound healing as assayed by earlier collagen deposition within the wound (as did M-1-P) and also markedly reduced scarring. The organisation of the collagen within the wound was greatly improved and the anti-scarring effect of M-6-P was better than in the wounds treated by a single injection on days 0, 1 and 2. These data suggest that more frequent application of mannose-6-phosphate on the first 3 days following wounding gives an improved until-scarring effect. No other treatment gave any anti-scarring effect.

EXAMPLE 6

This Example compares the effects of other phosphorylated sugars. This experiment was similar in design to all previous. Wounds were either unmanipulated (control) or treated by injection with 20 mM glycerol-3-phosphate, 20 mM galactose-6-phosphate, 20 mM mannose-6-phosphate or 20 mM galactose. The wounds were harvested on days 7 and 14 and 6 and 8 weeks after wounding. Two groups of animals were studied, those which were injected every 8 hours on days 0, 1 and 2 after wounding and those injected once on days 0, 1 and 2 post wounding. All histological sections were analysed by connective tissue staining and immunocytochemistry as previously described.

The results confirmed that application of 20 millimolar M-6-P at 8 hourly intervals on days 0, 1 and 2 after wounding, gave the best results. Wound healing was accelerated by early deposition of collagen within the wound and the treatment had marked anti-scarring activity. The wounds showed a more normal organisation of collagen fibrils within the dermis.

Galactose, galactose-6-phosphate and glycerol-3-phosphate showed no effect, wounds being similar, or if anything, slightly worse, than the control in terms of speed of healing and final scarring result.

I claim:

1. A method of treating a mammal in order to prevent or mitigate a fibrotic disorder associated with accumulation of extracellular matrix and with elevated levels of transforming growth factor $\beta1$ or $\beta2$, which method comprises administering to said mammal in need of such treatment an effective dose to combat said disorder of mannose-6- or 1-phosphate or a pharmaceutically acceptable salt or bio-precursor thereof.

2. The method of claim 1 wherein the fibrotic disorder is a skin wound.

3. The method of claim 1 wherein the fibrotic disorder is in the eye.

4. The method of claim 1 wherein the treatment is to accelerate wound healing.

5. A method of treating a mammal having a wound which comprises administering to the wound an effective dose to accelerate wound healing of mannose-6-phosphate or a pharmaceutically acceptable salt or bio-precursor thereof.

6. A cream or gel for tropical application comprising mannose-6- or 1-phosphate or a pharmaceutically acceptable salt or bio-precursor thereof and a pharmaceutically acceptable vehicle or carrier.

7. A wound dressing incorporating mannose-6- or 1-phosphate or a pharmaceutically acceptable salt or bio-precursor thereof.

8. A wound dressing according to claim 7 in the form of a bandage, sticking plaster, absorbent pad or polymeric dressing for positioning against a wound.

9. An implant material containing a sustained release formulation of mannose-6- or 1-phosphate or a pharmaceutically acceptable salt or bio-precursor thereof and a physiologically acceptable carrier.

10. The method of claim 4 using a wound dressing or a topically applied cream or gel incorporating mannose-6-phosphate or a pharmaceutically acceptable salt or bio-precursor thereof.

* * * * *